(12) United States Patent
Otsuka et al.

(10) Patent No.: US 6,509,490 B2
(45) Date of Patent: Jan. 21, 2003

(54) METHOD OF PURIFYING ISOPHTHALONITRILE

(75) Inventors: Susumu Otsuka, Niigata (JP); Takuji Shitara, Niigata (JP); Fumisada Kosuge, Niigata (JP); Kazuhiko Amakawa, Niigata (JP)

(73) Assignee: Mitsubishi Gas Chemical Co. Inc., Tokyo (JP)

( * ) Notice: Subject to any disclaimer, the term of this patent is extended or adjusted under 35 U.S.C. 154(b) by 0 days.

(21) Appl. No.: 09/953,409

(22) Filed: Sep. 17, 2001

(65) Prior Publication Data

US 2002/0035287 A1 Mar. 21, 2002

(30) Foreign Application Priority Data

Sep. 21, 2000 (JP) ........................................ 2000-287435

(51) Int. Cl.[7] ............................................. C07C 253/34
(52) U.S. Cl. ....................................................... 558/302
(58) Field of Search .......................................... 558/302

(56) References Cited

FOREIGN PATENT DOCUMENTS

GB          803172          * 10/1958

OTHER PUBLICATIONS

A copy of this reference is not being sent with the office action because the reference was not used in a rejection against the claims at issue.*

* cited by examiner

Primary Examiner—Joseph K. McKane
Assistant Examiner—Rebecca Anderson
(74) Attorney, Agent, or Firm—Antonelli, Terry, Stout, & Kraus LLP

(57) ABSTRACT

In a method for separating isophthalonitrile from a gas produced by causing m-xylene to react with ammonia and oxygen-containing gas in the presence of a catalyst, the gas is brought into contact with an organic solvent having a boiling point lower than that of isophthalonitrile; a liquid in which isophthalonitrile is trapped in a trapping step is distilled, to thereby recover isophthalonitrile and the organic solvent from the top of the column and separate at the bottom of the column impurities having boiling points higher than that of isophthalonitrile; and the organic solvent is recovered from the top of the rectification column and liquefied isophthalonitrile of high purity is recovered at the bottom of the column. Thus, loss of isophthalonitrile and plugging of a vacuum-evacuation system caused by isophthalonitrile migrating from a condensation system during distillation under reduced pressure can be prevented, and high-purity isophthalonitrile can be produced at high yield constantly for a long period of time.

5 Claims, 1 Drawing Sheet

METHOD OF PURIFYING ISOPHTHALONITRILE

BACKGROUND OF THE INVENTION

1. Field of the Invention

The present invention relates to a method of purifying isophthalonitrile including separating isophthalonitrile from a gas produced through reaction of m-xylene with ammonia and an oxygen-containing gas in the presence of a catalyst. Isophthalonitrile is useful as a raw material for producing synthetic resins and agrochemicals and an intermediate material for producing compounds such as amines and isocyanates.

2. Background

A method of reacting, in the presence of a catalyst, an organic-substituent-containing carbon-ring or heterocyclic compound with ammonia and an oxygen-containing gas is called ammoxidation, and is generally employed for producing nitrile compounds through a vapor-solid fluidized catalytic process.

A variety of methods for separating a nitrile compound from a gas produced through ammoxidation have already been known. For example, *Chemical Engineering* (November 1971, pp. 53–55) discloses a method for depositing isophthalonitrile, in which a gas produced through ammoxidation of m-xylene so as to produce isophthalonitrile is introduced into a scrubber and is cooled with water, then the obtained slurry of isophthalonitrile is introduced into a filter, to thereby isolate crystals of isophthalonitrile, and the crystals are dehydrated and dried, to thereby yield a final product.

Process Handbook (published in 1976, edited by The Japan Petroleum Institute) discloses the MGC-Badger isophthalonitrile process, in which isophthalonitrile contained in a gas produced through reaction is trapped by an organic solvent; the isophthalonitrile-trapped liquid is transferred to a solvent recovery column for the removal of solvent from the column top and crude isophthalonitrile is recovered from the bottom; and the crude isophthalonitrile is supplied to a rectification column, whereby purified isophthalonitrile is recovered from the column top.

In the method described in *Chemical Engineering* in which a gas produced through ammoxidation of m-xylene so as to produce isophthalonitrile is introduced into a scrubber and is cooled with water, by-products generated during ammoxidation are also deposited with isophthalonitrile. Thus, an additional purification step is required in order to obtain isophthalonitrile of high purity.

The method described in Process Handbook employing trapping by an organic solvent enables obtaining of high-purity isophthalonitrile. However, the method poses the following problems among others. (1) When a sublimable high-melting-point substance such as isophthalonitrile is separated through distillation under reduced pressure and removed from the top of the distillation column, isophthalonitrile may be solidified due to overcooling, since the condensation temperature and the melting point are close to each other in a high vacuum. (2) Due to high-temperature operation, vapor pressure of isophthalonitrile becomes high, and isophthalonitrile migrates to a vacuum evacuation system, to thereby deposit crystals thereof and cause plugging. (3) To prevent this, there must be taken measures including provision of a scrubber between the condensation section and the vacuum evacuation system. (4) Generally, in the presence of impurities such as high-boiling-point by-products generated during ammoxidation, ammoxidation catalyst, and metallic components, isophthalonitrile is unstable to heat and readily undergoes undesirable change or deterioration. Thus, when isophthalonitrile is exposed to high temperature during distillation, significant portions of isophthalonitrile are lost.

SUMMARY OF THE INVENTION

Thus, an object of the present invention is to provide a method for producing high-purity isophthalonitrile at high yield constantly for a long period of time in an industrially advantageous manner while, during purification through distillation of isophthalonitrile produced by ammoxidation, loss of isophthalonitrile is minimized and plugging due to deposition of crystals of isophthalonitrile from a condensation to a vacuum evacuation system is prevented.

In an attempt to solve the aforementioned problems, the present inventors have carried out extensive studies focusing on the methodology for producing isophthalonitrile, and have found that by trapping isophthalonitrile contained in a gas produced through ammoxidation by an organic solvent having a boiling point lower than that of isophthalonitrile; removing high-boiling-point impurities in a first distillation step; and in a second distillation step, separating the organic solvent and recovering isophthalonitrile from the bottom of the column, deterioration of isophthalonitrile can be suppressed, and provision of a special apparatus for preventing deposition of isophthalonitrile crystals in a vacuum evacuation system can be eliminated. The present invention has been accomplished on the basis of this finding.

Accordingly, the present invention provides a method for purifying isophthalonitrile including separating isophthalonitrile from a gas produced by causing m-xylene to react with ammonia and oxygen-containing gas in the presence of a catalyst, which method comprises the following steps:

a) a trapping step for bringing the gas into contact with an organic solvent having a boiling point lower than that of isophthalonitrile, to thereby trap isophthalonitrile in the organic solvent;

b) a high-boiling-point impurity separation step for distilling a liquid in which isophthalonitrile is trapped in the trapping step, to thereby recover isophthalonitrile and the organic solvent from the top of the column and separate at the bottom of the column impurities having boiling points higher than that of isophthalonitrile; and c) a rectification step for subjecting isophthalonitrile and the organic solvent resulting from the high-boiling-point impurity separation step to rectification, to thereby recover the organic solvent from the top of the column and recover liquefied isophthalonitrile of high purity at the bottom of the column.

DETAILED DESCRIPTION OF PREFERRED EMBODIMENTS

Figure 1:
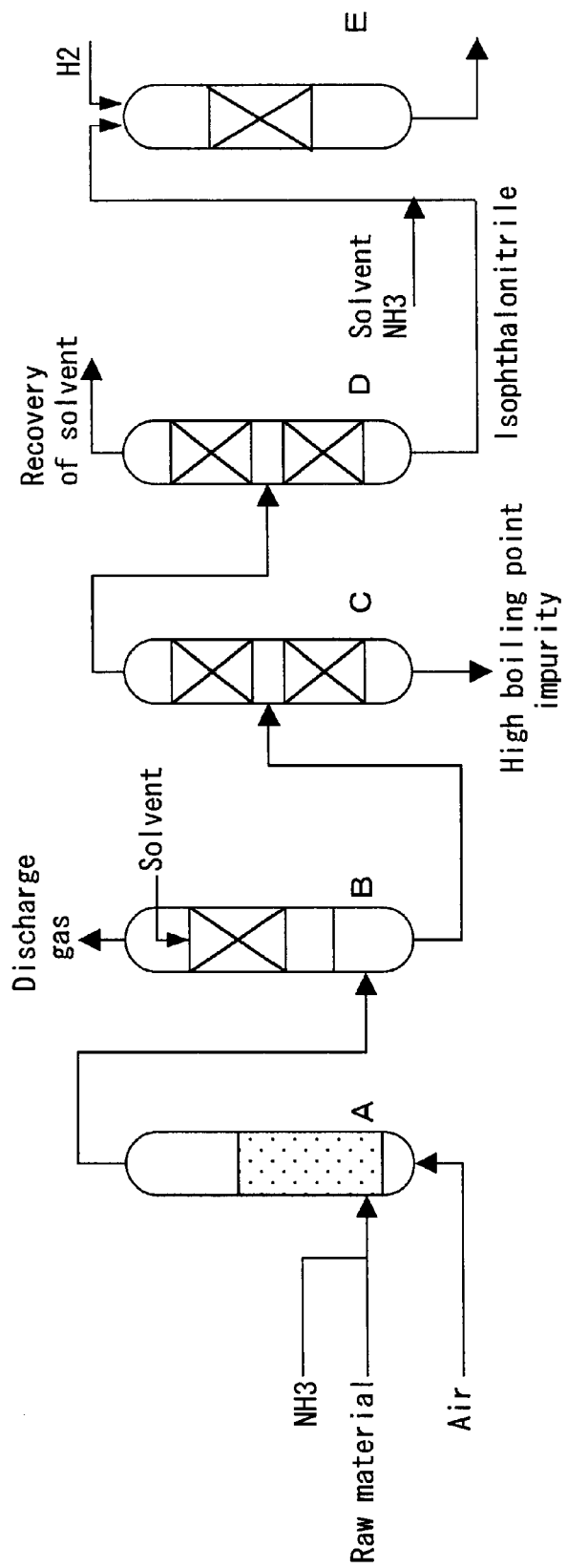
FIG. 1 is a flow chart illustrating one embodiment of the method for purifying isophthalonitrile according to the present invention, with A representing an ammoxidation reactor; B representing an isophthalonitrile trapping column; C representing an high-boiling-point impurity separation column; and D representing a rectification column.

In the present invention, during ammoxidation in which m-xylene is caused to react with ammonia and an oxygen-containing gas, there can be used known catalysts such as a catalyst containing V—Cr—B—Mo oxide disclosed in Japanese Patent Application Laid-Open (kokai) No. Heisei 11(1999)-209332 and a catalyst containing Fe—Sb—V oxide disclosed in Japanese Patent Application Laid-Open (kokai) No. Heisei 9(1997)-71561.

The oxygen-containing gas to be used in ammoxidation is typically air, which may be enriched with oxygen. A diluent such as nitrogen or carbon dioxide gas may also be used in combination. Oxygen is used in an amount by mol at least three times, preferably 4–100 times that of m-xylene serving as a raw material. When the amount of oxygen is less than the lower limit, yield of isophthalonitrile decreases, whereas when the amount is in excess of the upper limit, space-time yield decreases.

When ammoxidation is performed by use of air, the concentration of m-xylene contained in a raw material gas to be fed to the reactor is 0.2–10 vol. %, preferably 0.5–5 vol. %. When the concentration is less than the lower limit, yield of isophthalonitrile decreases, whereas when the concentration is in excess of the upper limit, space-time yield decreases.

Ammonia of industrial grade may be used as a raw material. Ammonia is used in an amount by mol of 2–20 times, preferably 6–15 times, that of m-xylene. When the amount of ammonia is less than the lower limit, yield of isophthalonitrile decreases, whereas when the amount is in excess of the upper limit, space time yield decreases.

Since ammoxidation generates a large amount of heat of reaction, the reaction is carried out preferably in a gas-phase-fluidized manner so as to attain a uniform temperature profile in the reactor, and a variety of fluidized-bed reactors can be employed. Ammonia may be supplied in the form of a mixture with m-xylene. In this case, a portion of an oxygen-containing gas may be added to the mixture of ammonia and m-xylene, with care being exerted so that the composition of the mixture does not fall within the explosion region, and the resultant mixture may be supplied to the reactor.

The temperature of ammoxidation is 300–500° C., preferably 330–470° C. When the reaction temperature is lower than the lower limit, percent conversion decreases, whereas when the temperature is in excess of the upper limit, formation of by-products such as carbon dioxide gas and hydrogen cyanide gas increases, to thereby decrease the yield of isophthalonitrile. Ammoxidation may be performed under ambient pressure, reduced pressure, or pressurized conditions, and a pressure of approximately ambient pressure to 0.2 MPa is preferred. Although the time of contact between the reactive gas and a catalyst varies in accordance with the conditions such as reaction temperature and the mol ratio of fed ammonia or oxygen-containing gas to fed m-xylene, the time is typically 0.3–30 seconds.

In the present invention, firstly in the trapping step, a gas produced through ammoxidation and supplied from the outlet of the ammoxidation reactor is introduced to an isophthalonitrile trapping column, whereby the reactive gas is brought into contact with an organic solvent, to thereby dissolve isophthalonitrile in the solvent. Thus, unreacted ammonia and gases such as hydrogen cyanide, carbon dioxide, steam, carbon monoxide, nitrogen, and oxygen are separated.

The organic solvent to be used is at least one solvent species selected from among alkylbenzenes, heterocyclic compounds, aromatic nitriles, and heterocyclic nitrites, and has a boiling point lower than that of isophthalonitrile. Preferably, the organic solvent dissolves isophthalonitrile therein at a high solubility, and is inert to isophthalonitrile. An organic solvent of low boiling point increases the amount of solvent entrained with residual gas.

Examples of the organic solvent include m-xylene, pseudocumene, mesitylene, ethylbenzene, methylpyridine, benzonitrile, m-tolunitrile, and cyanopyridine. These compounds may be used singly or in combination. Of these, m-tolunitrile is most suited in the present invention.

In operation of the isophthalonitrile trapping column, the gas produced through ammoxidation is introduced into a liquid phase at the bottom of the column. The trapping column is operated under such a condition that the temperature of the liquid phase at the bottom of the column is lower than the boiling point of the bottom liquid. Although the pressure in the isophthalonitrile trapping column may be ambient pressure, reduced pressure, or elevated pressure, a pressure of ambient pressure to pressure for ammoxidation is typically employed. Components which have not been absorbed in the organic solvent; e.g., ammonia, hydrogen cyanide, carbon dioxide, steam, carbon monoxide, nitrogen, and oxygen, are discharged from the top of the column, while isophthalonitrile absorbed in the organic solvent is taken from the bottom of the column and forwarded to a high-boiling-point impurity separation step.

In the high-boiling-point impurity separation step, isophthalonitrile absorbed in the organic solvent undergoes distillation in a high-boiling-point impurity separation column. Thus, high-boiling-point impurities are separated from isophthalonitrile and removed from the bottom potion of the column, and isophthalonitrile and the organic solvent are recovered from the top of the column.

The recovered isophthalonitrile and the organic solvent are forwarded to a rectification step. The organic solvent and impurities having boiling points lower than that of isophthalonitrile are separated and removed from the top of the column, while isophthalonitrile in liquid form is recovered from the bottom of the column.

Supply from the high-boiling-point impurity separation column to the rectification column may be performed in a state of gas or a condensed liquid. However, the supply of gas state as generated vapor is advantageous, from the viewpoint of saving energy.

In the presence of impurities such as high-boiling-point by-products generated during ammoxidation, ammoxidation catalyst, and metallic components, isophthalonitrile is unstable to heat, and is readily deteriorated to cause amidation, polymerization, or the like. This undesirable change results in a loss of some amounts of isophthalonitrile during distillation, and the loss increases in proportion to the period of time during which crude isophthalonitrile is handled at high temperature and to the handling temperature. Thus, in order to obtain isophthalonitrile at high yield, separation of high-boiling-point impurities must be performed as rapidly as possible and at as low a temperature as possible.

According to the present invention, isophthalonitrile is separated in advance from high-boiling-point impurities in the high-boiling-point impurity separation step. Thus, the period of time during which isophthalonitrile contacts the high-boiling-point impurities under heat can be shortened. In addition, distillation can be performed in a high vacuum, to thereby lower the temperature in the high-boiling-point impurity separation column and prevent deterioration of isophthalonitrile.

In each column, distillation is carried out under reduced pressure. The pressure is predetermined such that isophthalonitrile is not deposited in the column.

In general, when a mixture containing a sublimable high-melting-point substance is subjected to distillation, the interior temperature of the distillation column is elevated to a temperature not lower than the melting point of the substance, to thereby prevent plugging caused by deposition of crystals. Moreover, in the case in which a sublimable high-melting-point substance and a solvent in an amount sufficient for dissolving the sublimable high-melting-point substance are together placed in the distillation column, deposition of crystals does not occur even through the operation temperature is not higher than the melting point of the substance. The distribution of isophthalonitrile concentration in a distillation column is determined in accordance with the composition of supplied liquid, conditions for distillation and separation of the bottom residue, and vapor-liquid equilibrium conditions, and the temperature profile varies in accordance with operation pressure. Since the solubility of isophthalonitrile in a solvent is univocally determined only by temperature, operation pressure affects isophthalonitrile to be deposited or not deposited in the distillation column. For example, when rectification of isophthalonitrile is carried out by use of m-tolunitrile serving as an organic solvent for trapping a target with the inside pressure of the rectification column being 4.2 kPa or lower, in the distillation column there is generated a region where the temperature is not higher than the melting point of isophthalonitrile and the isophthalonitrile concentration exceeds the solubility of isophthalonitrile in m-tolunitrile. In this region, isophthalonitrile is deposited, to thereby plug the column. In the case in which isophthalonitrile and an organic solvent are supplied in the form of vapor from the high-boiling-point impurity separation column to the rectification column, increase in pressure of the top of the rectification column requires a higher bottom temperature of the high-boiling-point impurity separation column, leading to an increase in the amount of deteriorated isophthalonitrile. Thus, the operation pressure of the distillation column is controlled to high vacuum within the range where isophthalonitrile is not deposited in the distillation column. Specifically, when m-tolunitrile is used as an organic solvent for trapping isophthalonitrile, the pressure in the distillation column is preferably 5–10 kPa.

According to the method of the present invention, no scrubber is required to be provided between the condensation system and the vacuum-evacuation system. This is because isophthalonitrile is in contact with a solvent in an amount sufficient for dissolving therein in the distillation column, and substantially no vapor pressure of isophthalonitrile, caused by a low temperature of the condensation section predominantly containing a solvent, prevents migration of isophthalonitrile to the vacuum-evacuation system.

According to the method of the present invention, impurities having boiling points higher than that of isophthalonitrile and contained in the gas produced through ammoxidation are removed by means of the high-boiling-point impurity separation column, and as a result, these impurities do not migrate into the rectification column. Thus, isophthalonitrile is subjected to high temperature in the co-presence of a substance which promotes deterioration of isophthalonitrile only for a limited time; i.e., only when isophthalonitrile is retained in the high-boiling-point impurity separation column, leading to a reduction in loss of isophthalonitrile caused by deterioration.

The method of the present invention will next be described with reference to FIG. 1. FIG. 1 is a flow chart illustrating one embodiment of the method for purifying isophthalonitrile according to the present invention.

In FIG. 1, a gas produced in an ammoxidation reactor A is supplied to an isophthalonitrile trapping column B. In the upper section of the trapping column, an absorption portion comprising plates or a packed layer is provided, and an organic solvent is fed through the upper section of the trapping column. By bringing the gas into contact with the organic solvent, isophthalonitrile and high-boiling-point impurities contained in the produced gas are trapped in the solvent. Components which have not been absorbed in the organic solvent; e.g., ammonia, hydrogen cyanide, carbon dioxide, steam, carbon monoxide, nitrogen, and oxygen, are discharged from the upper section of the column.

The organic liquid containing isophthalonitrile is transferred to a high-boiling-point impurity separation column C, whereby isophthalonitrile and the organic solvent are recovered from the top, and high-boiling-point impurities are discharged from the bottom. The recovered isophthalonitrile and the organic solvent are transferred to a rectification column D. The organic solvent is recovered from the top of the column, while isophthalonitrile is recovered from the bottom of the column.

As described in the Example below, according to the method of the present invention, in the course of separating and purifying isophthalonitrile through distillation of a solution in which isophthalonitrile is trapped from a gas produced through ammoxidation, loss of isophthalonitrile due to deterioration which—loss would otherwise occur at the bottom of the distillation column—can be suppressed, and migration of isophthalonitrile from the top of the rectification column can be suppressed.

Thus, according to the method of the present invention, provision of a special apparatus for preventing plugging from a condensation system to a vacuum evacuation system during distillation under reduced pressure can be eliminated, and high-quality isophthalonitrile can be produced at high yield constantly for a long period of time.

Also in the present invention, Supply from the high-boiling-point impurity separation column to the rectification column is performed while the supplied substance is in the form of vapor, leading to an industrial advantage from the viewpoint of energy savings.

EXAMPLES

The present invention will next be described in more detail by way of Example and Comparative Examples, which should not be construed as limiting the invention thereto.

<Preparation of Catalyst for Ammoxidation Reaction>

Vanadium pentoxide ($V_2O_5$) (229 g) was added to water (500 mL), to thereby yield a mixture, and an aliquot of oxalic acid (477 g) was added to the mixture with stirring at 80–90° C. so as to dissolve the vanadium compound, to thereby yield a solution of vanadium oxalate. Another aliquot of oxalic acid (963 g) was added to water (400 mL), and the resultant mixture was heated to 50–60° C. To the mixture, a solution of chromic anhydride ($CrO_3$) (252 g) in water (200 mL) was added under sufficient stirring so as to dissolve the components, to thereby yield a solution of chromium oxalate. The thus-yielded solutions were mixed at 50–60° C., to thereby prepare a V—Cr—containing solution. To the V—Cr—containing solution, a solution of phosphomolybdic acid ($H_3(PMo_{12}O_{40})\cdot 20H_2O$) (41.1 g) dissolved in water (100 mL) and a solution of potassium acetate ($CH_3COOK$) (4.0 g) dissolved in water (100 mL) were added. Subsequently, a 20 wt. % aqueous silica sol (containing 0.02 wt. % of $Na_2O$) (2,500 g) was added, to thereby yield a slurry.

Boric acid ($H_3BO_3$) (78 g) was added to the slurry, and the resultant mixture was concentrated by heating until the liquid amount became approximately 3,800 g. The thus-concentrated mixture containing catalyst components was dried by use of a spray drier while the inlet temperature and the outlet temperature were maintained at 250° C. and 130° C., respectively. The dried mixture was further dried by means of a drier at 130° C. for 12 hours, and the resultant mixture was calcined at 400° C. for 0.5 hours and at 550° C. for eight hours under air flow, to thereby obtain a catalyst to be used in a fluidized process. The obtained catalyst was found to have atomic proportions of V:Cr:B:Mo:P:Na:K= 1:1:0.5:0.086:0.007:0.009:0.020 and an effective catalyst component content of 50 wt. %.

Example 1

Ammoxidation; trapping of isophthalonitrile in an organic solvent; and distillation for separating and purifying isophthalonitrile were performed on the basis of the process flow shown in FIG. 1.

The catalyst (6 L) which had been prepared in the above-described manner was charged into an ammoxidation reactor A. After air, m-xylene (MX), and ammonia had been mixed and pre-heated to 350° C., the resultant mixture was fed to the reactor. The following feed conditions were employed: an amount of fed MX of 350 g/Hr; a mol ratio of $NH_3$/MX of 11; a mol ratio of $O_2$/MX of 5.4; and an SV of 630 $Hr^{-1}$. The temperature and the pressure for reaction were 420° C. and 0.2 MPa-G, respectively.

The gas produced through reaction and supplied from the top of the reactor was introduced into an isopthalonitrile trapping column B, whereby isohptalonitrile contained in the produced gas was trapped in m-tolunitrile serving as a solvent.

The isophthalonitrile trapping column, made of SUS 304, was equipped with a condenser at the upper section and a gas-bubbling inlet at the bottom section. The main body of the column had an inside diameter of 100 mm φ and a height of 800 mm, and the lower portion (450 mm) of the main body was provided with a double tube structure so as to allow steam heating.

Specifically, the gas produced through the aforementioned ammoxidation was subjected to a trapping process for two hours by use of m-tolunitrile (2 kg) charged into the trapping column and heated to 175° C., to thereby trap components. After completion of trapping, the liquid was found to have the following composition; i.e., m-tolunitrile (73.5 wt. %), isophthalonitrile (25 wt. %), cyanobenzamide (1 wt. %), and other components (0.5 wt. %).

The aforementioned liquid was supplied to a middle stage plate of a high-boiling-point impurity separation column C, and the gas produced through distillation carried out in the high-boiling-point impurity separation column C was supplied to a rectification column D. Distillation in the high-boiling-point impurity separation column C. was performed at a top pressure of 8 kPa, a top temperature of 164° C., and a bottom temperature of 204° C., and distillation in the rectification column D was performed at a top pressure of 6 kPa, a top temperature of 120° C., and a bottom temperature of 183° C. The thus-purified isophthalonitrile, which had been recovered from the bottom of the rectification column, had a purity of 99.93%. The percent recovery of isophthalonitrile including isophthalonitrile contained in a fraction from which the high-boiling-point impurity had been separated was 98%. In other words, the high-boiling-point impurity included 2% unrecovered isophthalonitrile.

Comparative Example 1

The procedure of Example 1 was repeated, to thereby obtain a liquid in which a gas produced through ammoxidation had been trapped. The liquid was subjected to distillation for purification. Briefly, the liquid was distillated in a first column, whereby organic solvent and a low-boiling-point fraction were separated. The bottom liquid of the first column was fed into a second distillation column, whereby a high-boiling-point impurity remaining in the bottom thereof was removed and isophthalonitrile was recovered from the top thereof. The second distillation was performed at a top pressure of 4 kPa, a top temperature of 173° C., and a bottom temperature of 191° C. However, a large amount of isophthalonitrile was splashed in a region from the condensation system to the vacuum-evacuation system, resulting in plugging the line and disturbing continuous operation.

Comparative Example 2

In Comparative Example 2, a scrubber was provided in the line between the condensation system and the vacuum-evacuation system provided in the second distillation column, so as to prevent plugging, and continuous operation was performed. The purified isophthalonitrile had a purity of 99.95%. However, the percent recovery of isophthalonitrie was 94%, and 2% among 6% unrecovered isophthalonitrile was collected by the scrubber. In other words, the high-boiling-point impurity included unrecovered isophthalonitrile (4%).

What is claimed is:

1. A method for purifying isophthalonitrile after separating isophthalonitrile from a gas produced by causing m-xylene to react with ammonia and oxygen-containing gas in the presence of a catalyst, which method comprises the following steps:

a) a trapping step for bringing the gas into contact with an organic solvent having a boiling point lower than that of isophthalonitrile, to thereby trap isophthalonitrile in the organic solvent;

b) a high-boiling-point impurity separation step for distilling a liquid in which isophthalonitrile is trapped in the trapping step, to thereby recover isophthalonitrile and the organic solvent from the top of the column and separate at the bottom of the column impurities having boiling points higher than that of isophthalonitrile; and c) a rectification step for subjecting isophthalonitrile and the organic solvent resulting from the high-boiling-point impurity separation step to rectification, to thereby recover the organic solvent from the top of the column and recover liquefied isophthalonitrile of high purity at the bottom of the column.

2. A method for purifying isophthalonitrile according to claim 1, wherein the isophthalonitrile and organic solvent resulting from the high-boiling-point impurity separation step are supplied in the form of vapor to a rectification column employed in the rectification step.

3. A method for purifying isophthalonitrile according to claim 1, wherein the organic solvent for trapping isophthalonitrile is at least one compound selected from alkylbenzenes, heterocyclic compounds, aromatic nitriles, and heterocyclic nitrites, and having a boiling point lower than that of isophthalonitrile.

4. A method for purifying isophthalonitrile according to claim 3, wherein the organic solvent for trapping isophthalonitrile is at least one compound selected from m-xylene, pseudocumene, mesitylene, ethylbenzene, methylpyridine, benzonitrile, m-tolunitrile, and cyanopyridine.

5. A method for purifying isophthalonitrile according to claim 4, wherein m-tolunitrile is employed as the organic solvent for trapping isophthalonitrile, and the rectification step employs a pressure of 5–10 kPa.

* * * * *